(12) United States Patent
Niconovich et al.

(10) Patent No.: US 7,169,792 B2
(45) Date of Patent: Jan. 30, 2007

(54) METHOD OF TREATING BACTERIAL INFECTIONS USING GEMIFLOXACIN OR A SALT THEREOF AND A β-LACTAM ANTIBIOTIC

(75) Inventors: Nancy Niconovich, Collegeville, PA (US); Stephen Rittenhouse, Collegeville, PA (US); Lynn McCloskey, Collegeville, PA (US); Kyong-Sook Paek, Taejon (KR); Mu-Yong Kim, Taejon (KR); Ha-Sik Youn, Taejon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/496,809

(22) PCT Filed: Nov. 29, 2002

(86) PCT No.: PCT/KR02/02248

§ 371 (c)(1),
(2), (4) Date: Jul. 15, 2004

(87) PCT Pub. No.: WO03/045390

PCT Pub. Date: Jun. 5, 2003

(65) Prior Publication Data

US 2005/0148571 A1 Jul. 7, 2005

(51) Int. Cl.
*A01N 43/442* (2006.01)
*A01N 43/40* (2006.01)
*A01N 43/76* (2006.01)

(52) U.S. Cl. .................. 514/299; 514/338; 514/370

(58) Field of Classification Search .......... 514/253.08, 514/299, 338, 370
See application file for complete search history.

(56) References Cited

FOREIGN PATENT DOCUMENTS

WO    WO 98/42705    * 10/1998

OTHER PUBLICATIONS

Ronald Arky, The Physicians' Desk Reference, 1997, 51 Edition, pp. 930, 1070-1073, and 1259-1261, for example.*

Wise R. and Andrews J.M., "The in-Vitro Activity and Tentative Breakpoint of Gemifloxacin, a new Fluoroquinolone", In: J. Antimivrob. Chemother., Nov. 1999, 44(5): pp. 679-688.

Zhang L. et al., "Fluoroquinolone Susceptibilities of Efflux-Mediated Multidrug-Resistant *Pseudomonas aeruginosa. Stenotrophomonas maltophilia* and *Burkholderia cepacia*." In: J. Antimicrob. Chemother., Oct. 2001, 48(4) : pp. 549-552.

Hoban D.J. et al., "A Comparative in Vitro Surveillance Study of Gemifloxacin Activities Against 2,632 Recent *Streptococcus pneumoniae* Isolates from Across Europe, North America, and South America. The Gemifloxacin Surveillance Study Research Group." In: Antimicrob. Agents Chemother., Nov. 2000., 44(11) : pp. 3008-3011.

Hoban D.J. et al., "Comparative in Vitro Activity of Gemifloxacin, Ciprofloxacin, Levofloxacin and Ofloxacin in a North American Surveillance Study." In: diagn. Microbiol. Infect. Dis., May-Jun. 2001, 40(102) : pp. 51-57.

Visalli M.A. et al., "Determination of Activities of Levofloxacin, Alone and Combined with Gentamicin,Ceftazdime, Cefpirome, and Meropenem, Against 124 Strains of *Pseudomonas aeruginosa* by Checkerboard and Time-Kill Methodology." In: Antimicrob. Agents Chemother., Apr. 1998., 42(4) : pp. 953-955.

Aubert G. et al., "In Vitro Effect of New Fluoroquinolones and Betalactamines Combinations Against Enterococci." In: Pathol. Biol., Dec. 1999. 39(10) : pp. 1006-1008.

* cited by examiner

*Primary Examiner*—San-ming Hui
(74) *Attorney, Agent, or Firm*—Birch, Stewart, Kolasch & Birch, LLP

(57) ABSTRACT

The present invention relates to a method of treating antibacterial infections which method comprises the separate, simultaneous or sequential administration to a patient in need thereof, of an effective amount of gemifloxacin or a salt thereof and a β-lactam antibiotic.

8 Claims, No Drawings

METHOD OF TREATING BACTERIAL INFECTIONS USING GEMIFLOXACIN OR A SALT THEREOF AND A β-LACTAM ANTIBIOTIC

TECHNICAL FIELD

This invention relates to a novel method of treating bacterial infections using a combination of antibacterial agents, more particularly gemifloxacin or a salt thereof and a β-lactam antibiotic.

BACKGROUND ART

Gemifloxacin [(R,S)-7-(3-aminomethyl-4-methoxyimino-pyrrolidin-1-yl)-1-cyclopropyl-6-fluoro-4-oxo-1,4-dihydro-1,8-naphthyridine-3-carboxylic acid] is a fluoroquinolone antibacterial agent which has enhanced in vitro antibacterial activity against Gram-positive bacteria, whilst retaining excellent activity against Gram negative bacteria. Without intending to be bound or limited by theory, gemifloxacin is believed to act via inhibition of bacterial topoisomerase II and IV. Gemifloxacin is highly selective for bacterial rather than human topoisomerase II.

EP 688772 discloses novel naphthyridine carboxylic acid derivatives, including gemifloxacin. WO 98/42705 discloses gemifloxacin mesylate and hydrates thereof including the sesquihydrate.

There still remains the need for improved methods of treating bacterial infections. In particular, infections caused by *Psezudomonas aeruginosa* continue to pose a therapeutic problem. In clinical practice, the combination of β-lactam antibiotic and aminoglycoside antibacterial agents has been shown to have an improved efficacy for the treatment of infections caused by *P. aeruginosa*. However, increased resistance of *P. aeruginosa* to aminoglycosides, coupled with their potential for nephrotoxicity, means there still remains the need for alternative treatments.

Other examples of infections for which improved methods of treatment are needed include those caused by *Enterococcus faecalis*, *Staphylococcus saprophyticus*, and *Escherichia coli*.

DISCLOSURE OF THE INVENTION

The present invention provides a method of treating bacterial infections which method comprises the separate, simultaneous or sequential administration to a patient in need thereof, of an effective amount of gemifloxacin or a salt thereof and a β-lactam antibiotic. The patient may be human or animal, and in a preferred embodiment is human.

The present inventors have found combinations of gemifloxacin or a salt thereof and a β-lactam antibiotic that provide an antibacterial regimen which has a broader spectrum of activity than either agent alone. In particular, such combinations have been found that exhibit synergistic activity against several clinical isolates of *Pseudomonas aeruginosa*, as well as reference strains of *Enterococcus faecalis*, *Staphylococcus saprophyticus*, or *Escherichia coli*, relative to either agent alone.

Suitable salts of gemifloxacin include those described in WO 98/42705, EP 688772, and U.S. Pat. No. 5,776,944. In particular embodiments, the salt of gemifloxacin is selected from the mesylate and hydrates thereof, in particular the sesquihydrate as described in WO 98/42705.

Suitable β-lactam antibiotics for use in the method of the invention include the penicillins: e.g., amoxycillin, ampicillin, apalcillin, aspoxicillin, azidocillin, azlocillin, aztreonam, benzylpenicillin, bacampicillin, carbenicillin, cloxacillin, cyclacillin, dicloxicillin, epicillin, flucloxacillin, lenampicillin, mecillinam, methicillin, mezlocillin, phenoxymethylpenicillin, piperacillin, pivampicillin, propicillin, sulbenicillin, talampicillin, and ticarcillin; and the cephalo-sporins: e.g., cefaclor, cefadroxil, cefatrizine, cefclidine, cefamandole, cefazolin, cefbuperazone, cefcanel daloxate, cefdinir, cefepime, cefetamet pivoxil, cefixime, cefminox, cefminoxime, cefinetazole, cefonicid, cefoperazone, cefotaxime, cefotetan, cefotiam, cefotiam hextetil, cefoxitin, cefpimizole, cefpiramide, cefpirome, cefpodoxime proxetil, cefprozil, cefiazidime, ceftibuten, ceftizoxime, ceftriaxone, cefuroxime axetil, cefuroxime, cephacetrile, cephalexin, cephaloridine, cephalothin, cephamanadole nafate, cephapirin, cephoperazone, cefsulodin, cefuzonam, cephradine, loracarbef, DQ 2556, ME 1207, S-1006, SCE-2787 and moxalactam.

In particular embodiments, the β-lactam antibiotic for use in the method of the invention is selected from amoxicillin and the cephalo-sporins, e.g. cefotaxime, ceftazidime, and cefaclor.

The β-lactam antibiotics referred to herein may be in the form of the free acids or pharmaceutically acceptable salts or in-vivo hydrolysable esters.

Gemifloxacin or a salt thereof and a β-lactam antibiotic, or a composition comprising same, may be used in accordance with the present invention to modulate metabolism of bacteria (e.g., clinical isolates, reference bacteria, pathogenic bacteria) and/or to treat infections caused by such bacteria. Clinical isolates or reference bacteria include *Streptococcus pneumoniae* (e.g., ATCC 49619), *Haemophilus influenzae* (e.g., ATCC 49247), *Moraxella catarrahalis* (e.g., 1502), *Staphylococcus aureus* (e.g., ATCC 29213), *Staphylococcus saprophyticus* (e.g., 662), *Klebsiella pneumoniae* (e.g. E70), *Proteus vulgaris* (e.g., ATCC 13315), *Enterococcus faecalis* (e.g., ATCC 29212), *Escherichia coli* (e.g., ATCC 25922), and *Pseudomonas aeruginosa* (e.g., ATCC 27853, 6016, 6156, 6168, P003, 6140, PA018R, 6003, 6021, 6030, 6045, 6047, 6113, 6123, 6173, P032, P036, P039, 6003, 6021, 6034, 6102, 6104, 6113, 6170, 6173, 6178, P020, P022, P028, P033, P035, P039, P045, P049, P050, P061, P070, P071).

Particular embodiments of the invention include the following treatment regimens:
a) gemifloxacin and ceftazidime for the treatment of infections caused by *Pseudomonas aeruginosa*;
b) gemifloxacin and cefotaxime for the treatment of infections caused by *Enterococcus faecalis*;
c) gemifloxacin and amoxicillin for the treatment of infections caused by *Staphlylococcus saprophyticus*; and
d) gemifloxacin and cefaclor for the treatment of infections caused by *Escherichia coli*.

Suitably, gemifloxacin or a salt thereof and the β-lactam antibiotic are administered in a ratio of from about 10:1 to about 1:10, more suitably about 5:1 to 1:5, typically about 2:1 w/w, expressed as the weight of the free acid and free base respectively.

Suitably, the administration is substantially simultaneous. This may conveniently be achieved by the co-administration of separate pharmaceutical compositions comprising gemifloxacin or a salt thereof and a β-lactam antibiotic. Such separate compositions may be usefully provided as a kit comprising a gemifloxacin, or a salt thereof, composition and a β-lactam antibiotic composition. The kit preferably contains sufficient dosages of gemifloxacin, or a salt thereof, and the β-lactam antibiotic for a single course of therapy for the particular infection to be treated, together with instructions for administration.

Accordingly the present invention also provides a kit of parts for use in treating bacterial infections in mammals which comprises an antibacterially effective amount of (a) a pharmaceutical composition comprising gemifloxacin or a salt thereof, and a pharmaceutically acceptable carrier, and (b) a pharmaceutical composition comprising a β-lactam antibiotic and a pharmaceutically acceptable carrier.

Alternatively gemifloxacin, or a salt thereof, and a β-lactam antibiotic may be formulated together and administered in a single composition.

Accordingly in a further aspect the present invention further provides a pharmaceutical composition comprising gemifloxacin or a salt thereof, a β-lactam antibiotic, and a pharmaceutically acceptable carrier.

The present invention also includes the use of gemifloxacin or a salt thereof in the manufacture of a medicament for use in combination with a β-lactam antibiotic in the treatment of bacterial infections.

The invention further provides gemifloxacin or a salt thereof in combination with a β-lactam antibiotic for use in the treatment of bacterial infections.

The invention also includes a method of treating bacterial infections comprising administering to a mammal in need of such treatment, a therapeutically effective amount of gemifloxacin or a salt thereof and a β-lactam antibiotic. In preferred embodiments, the treatment comprises administering therapeutically effective amounts of gemifloxacin or a salt thereof and a β-lactam antibiotic, wherein the activity of the antibiotics against the bacterial infection is synergistic.

The invention also includes a method of modulating the metabolism of bacteria, comprising contacting the bacteria with an antibacterially effective amount of gemifloxacin and a salt thereof and a β-lactam antibiotic (optionally in the form of an antibacterially effective composition or kit of compositions, as described herein). Modulating metabolism suitably comprises inhibiting growth of the bacteria or killing the bacteria. Contacting the bacteria may suitably comprise the step of introducing the antibiotics or composition or kit of compositions comprising same into a mammal. In preferred embodiments, the method comprises contacting the bacteria with an antibacterially effective amount of gemifloxacin or a salt thereof and a β-lactam antibiotic, or composition or kit of compositions comprising same, wherein the activity of the antibiotics against the bacteria is synergistic.

Suitable formulations comprising gemifloxacin include those described in WO 98/42705, EP 688772, and U.S. Pat. No. 5,776,944.

Suitable formulations comprising a β-lactam antibiotic are well known in the art and are readily available commercially.

Gemifloxacin or a salt thereof may be formulated with a β-lactam antibiotic and standard pharmaceutical carriers or diluents according to conventional procedures well known in the art. These procedures may involve mixing, granulating and compressing or dissolving the ingredients as appropriate to the desired preparation.

The invention further provides a method for the preparation of a pharmaceutical composition comprising gemifloxacin or a salt thereof and a β-lactam antibiotic which method comprises admixing the combination of gemifloxacin or a salt thereof and a lactam antibiotic and a pharmaceutically acceptable carrier.

The invention further provides a formulation for the treatment of bacterial infections comprising gemifloxacin or a salt thereof and β-lactam antibiotic. In preferred embodiments, the formulation comprises an amount of gemifloxacin or a salt thereof and β-lactam antibiotic wherein the activity of the antibiotics in treating the bacterial infection is synergistic.

The invention further provides the use of a formulation comprising gemifloxacin or a salt thereof and a β-lactam antibiotic in the manufacture of a medicament for the treatment of bacterial infections.

In the compositions, kits, and methods of the present invention the bacterial infection is preferably one caused by *P. aeruginosa, S. saprophyticus, E. faecalis* or *E. coli*.

Infections caused by *P. aeruginosa* include wound infections, urinary tract infections and respiratory tract infections, together with general infections in an immunocompromised patient. Infections caused by *S. saprophyticus* and *E. faecalis* include urinary tract infections and general infections in an immunocompromised patient. Infections caused by *E. coli* include urinary tract infections.

The contacting step and administration step in any of the methods of the invention may be performed in many ways that will be readily apparent to the skilled artisan. However, it is preferred that the contacting step and administration step is a provision of a composition comprising gemifloxacin or a salt thereof and a β-lactam antibiotic, or in the case of a kit according the present invention, a composition comprising gemifloxacin or a salt thereof and a composition comprising a β-lactam antibiotic, to a human patient in need of such composition(s), or directly to bacteria in culture medium or buffer.

For example, when contacting a human patient or contacting said bacteria in a human patient or in vitro, the composition(s) comprising gemifloxacin or a salt thereof and/or a β-lactam antibiotic, preferably pharmaceutical composition(s), may be administered in any effective, convenient manner including, for instance, administration by topical, oral, anal, vaginal, intravenous, intraperitoneal, intramuscular, subcutaneous, intranasal or intradermal routes among others.

It is also preferred that these compositions be employed in combination with a non-sterile or sterile carrier or carriers for use with cells, tissues or organisms, such as a pharmaceutical carrier suitable for administration to a subject. Such compositions comprise, for instance, a therapeutically effective amount of gemifloxacin or a salt thereof, and/or a β-lactam antibiotic, a pharmaceutically acceptable carrier or excipient, and optionally a media additive. Such carriers may include, but are not limited to, saline, buffered saline, dextrose, water, glycerol, ethanol and combinations thereof. The formulation(s) should suit the mode of administration.

In therapy or as a prophylactic, the gemifloxacin or salt thereof and β-lactam antibiotic are preferably administered to an individual as an injectable composition (including compositions comprising both antibiotics, or separate injectable compositions comprising one or the other antibiotic), for example as a sterile aqueous dispersion, preferably an isotonic one.

Alternatively, the gemifloxacin or salt thereof and β-lactam antibiotic in the methods of the invention may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the antibacterially effective amount is a daily dosage level of the active agent from 0.001 mg/kg to 10 mg/kg, typically around 0.1 mg/kg to 1 mg/kg, preferably about 1 mg/kg. A physician, in any event, will determine an actual dosage that is most suitable for an individual and will vary with the age, weight and response of the particular individual. The above dosages are exemplary of the average case. There can, of course, be individual instances where higher or lower dosage ranges are merited, and such are within the scope of this invention. It is preferred that the dosage is selected to modulate metabolism of the bacteria in such a way as to inhibit or stop growth of said bacteria or by killing said bacteria. The skilled artisan may identify this amount as provided herein as well as using other methods known in the art, e.g. by the application MIC tests.

A further embodiment of the invention provides for the contacting step or administration step of the methods to further comprise contacting an in-dwelling device in a patient. In-dwelling devices include, but are not limited to, surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

The gemifloxacin or salt thereof and β-lactam antibiotic, or composition or kit of compositions of the invention, may be administered by injection to achieve a systemic effect against relevant bacteria, shortly before insertion of an in-dwelling device. Treatment may be continued after surgery during the in-body time of the device. In addition, the composition or kit of compositions could also be used to broaden perioperative cover for any surgical technique to prevent bacterial wound infections.

In addition to the therapy described above, gemifloxacin or a salt thereof and a lactam antibiotic, or composition or kit of compositions used in the methods of this invention may be used generally as a wound treatment agent to prevent adhesion of bacteria to matrix proteins, exposed in wound tissue and for prophylactic use in dental treatment as an alternative to, or in conjunction with, antibiotic prophylaxis.

Alternatively, gemifloxacin or a salt thereof and a β-lactam antibiotic, or composition or kit of compositions of the invention may be used to bathe an indwelling device immediately before insertion. The active agent will preferably be present at a concentration of 1 μg/ml to 10 mg/ml for bathing of wounds or indwelling devices.

All documents cited or referred to herein, including issued patents, published and unpublished patent applications, and other publications are hereby incorporated herein by reference as though fully set forth.

BEST MODE FOR CARRYING OUT THE INVENTION

The invention will now be described by the following examples which are illustrative and not intended to limit the invention hereinbefore described.

EXAMPLES

The potential for the combination therapy of gemifloxacin and a β-lactam antibiotic was investigated.

1) The combined effect of gemifloxacin and cefotaxime was investigated in *E. faecalis* by using a checkerboard titration method. Evaluation for synergistic activity was carried out by calculation of fractional inhibitory concentrations (FICs) according to the method of Eliopoulos et al (1996, Antimicrobial Combinations, *Antibiotics in Laboratory Medicine*, Victor Lorian, 4th Edition, pp 337–338, Baltimore, Md., Williams and Wilkins).

*E. faecalis* ATCC 29212 was obtained from the SmithKline Beecham Anti-Infectives Research Culture Collection and stored at −80° C. in 10% glycerol. Before testing, the isolate was passaged onto agar plates (trypticase soy agar containing 5% sheeps blood) from the frozen stock for two consecutive days. Cation adjusted Mueller Hinton broth (BBL, Cockeysville, Md.) was used for the isolate.

Checkerboard microtitre broth dilution plates were prepared using the Hamilton MicroLab AT Plus system (Reno, Nev.). Two-fold serial dilutions (50 μl) of cefotaxime were made in columns 1 through 11 of a microtitre plate. Two-fold serial dilutions of gemifloxacin were prepared manually and the MicroLab AT Plus was used to dispense 25 μl of gemifloxacin at each concentration into rows A through G of the microtitre plate. The concentration range tested varied for each drug/organism combination to encompass the MIC endpoints of the individual components. Column 12 contained two fold serial dilutions of gemifloxacin only, and row H contained two fold serial dilutions of cefotaxie only. The last well (H) in column 12 was used as a positive growth control well, containing only medium and test isolate.

The bacteria were diluted to a 0.5 McFarland standard and then further diluted 1/50. Each well was inoculated with 25 μl of the isolate to give a final inoculum density of approximately $5 \times 10^5$ cfu/ml. The MicroLab AT Plus 2 was used to add the inoculum to the microtitre plates. After inoculation, the plates were covered with a 96 well microtitre plate lid and incubated at 35° C. in ambient air for 20–24 hours. A 10 μl aliquot of the inoculum was plated on trypticase soy agar containing 5% sheep blood to determine the purity of the final test inoculum.

Following incubation, a microtitre mirror reader (Cooke Instruments Ltd., England) was used to assist in determining the microdilution MIC endpoints. The MIC was determined as the lowest concentration of compound that inhibited visible growth of the organism.

The Fractional Inhibitory Concentrations (FICs) were calculated using the following formula:

$$(A)/(MICA)+(B)/(MICB)=FICA+FICB=FIC\text{Index}$$

wherein:
A is the MIC of drug A in the presence of drug B
B is the MIC of drug B in the presence of drug A
MIC A is the MIC of the organism to drug A alone
MIC B is the MIC of the organism to drug B alone
FIC A is the fractional inhibitory concentration of drug A
FIC B is the fractional inhibitory concentration of drug B The FIC indices were interpreted using the following criteria:
≦0.5=Synergy
>0.5–1=Additive
>1–2=Indifference
>2=Antagonism Gemifloxacin/cefotaxime combinations exhibited a synergistic effect against E. faecalis ATCC 29212.

| gemifloxacin μg/ml | 0.008 | — | — | — |
|---|---|---|---|---|
| cefotaxime μg/ml | — | 64 | 32 | 16 |
| gemifloxacin MIC μg/ml | — | 0.008 | 0.008 | 0.008 |
| cefotaxime MIC μg/ml | 16 | — | — | — |
| FIC | 0.31 | 0.5 | 0.38 | 0.31 |
| gemifloxacin MIC | 0.03 | 0.03 | 0.03 | 0.03 |
| cefotaxime MIC | 256 | 256 | 256 | 256 |

Other gemifloxacin/cefotaxime combinations tested exhibited an additive or indifferent effect against E. faecalis ATCC 29212. In wells where no growth was observed and the MIC of one of the agents had been achieved or exceeded, the result was reported as inhibited.

2) S. saprophyticus 662 was obtained from the SmithKline Beecham Anti-Infectives Research Culture Collection and stored at −80° C. in 10% glycerol. Before testing, the isolate was passaged onto agar plates (trypticase soy agar containing 5% sheeps blood) from the frozen stock for two consecutive days. Cation adjusted Mueller Hinton broth (BBL, Cockeysville, Md.) was used for the isolate.

The combined effect of gemifloxacin and amoxicillin was investigated in S. saprophyticus 662 by using the checkerboard titration method described in Example 1.

FIC Indices were calculated and interpreted as in Example 1. A gemifloxacin/amoxicillin combination exhibited a synergistic effect against S. saprophyticus 662.

| gemifloxacin μg/ml | 0.004 | — |
|---|---|---|
| amoxicillin μg/ml | — | 0.125 |
| gemifloxacin MIC μg/ml | — | 0.004 |
| amoxicillin MIC μg/ml | 0.125 | — |
| FIC | 0.50 | 0.5 |
| gemifloxacin MIC | 0.016 | 0.016 |
| cefotaxime MIC | 0.5 | 0.5 |

Other gemifloxacin/amoxicillin combinations tested exhibited an additive or indifferent effect against S. saprophyticus 662. In wells where no growth was observed and the MIC of one of the agents had been achieved or exceeded, the result was reported as inhibited.

3) E. coli ATCC 25922 was obtained from the SmithKline Beecham Anti-Infectives Research Culture Collection and stored at −80° C. in 10% glycerol. Before testing, the isolate was passaged onto agar plates (trypticase soy agar containing 5% sheeps blood) from the frozen stock for two consecutive days. Cation adjusted Mueller Hinton broth (BBL, Cockeysville, Md.) was used for the isolate.

The combined effect of gemifloxacin and cefaclor was investigated in E. coli ATCC 25922 by using the checkerboard titration method described in Example 1. FIC Indices were calculated and interpreted as in Example 1.

A gemifloxacin/cefaclor combination exhibited a synergistic effect against E. coli 25922.

| gemifloxacin μg/ml | 0.002 | — |
|---|---|---|
| cefaclor μg/ml | — | 1 |
| gemifloxacin MIC μg/ml | — | 0.002 |
| cefaclor MIC μg/ml | 1 | — |
| FIC | 0.50 | 0.5 |
| gemifloxacin MIC | 0.008 | 0.008 |
| cefaclor MIC | 4 | 4 |

Other gemifloxacin/cefaclor combinations tested exhibited an additive or indifferent effect against E. coli 25922. In wells where no growth was observed and the MIC of one of the agents had been achieved or exceeded, the result was reported as inhibited.

4) The synergistic activity of gemifloxacin in combination with ceftazidime was investigated in 27 clinically isolated P. aeruginosa by using a checkerboard titration method, and compared with that of a ciprofloxacin/ceftazidime combination. Gemifloxacin/ceftazidime combination showed a good synergistic effect against P. aeruginosa and had better synergistic profiles than the ciprofloxacin/ceftazidime combination. For the gemifloxacin/ceftazidime combination, a synergistic effect (FIC≦0.5) was observed with 13 of 27 strains and an additive or indifferent effect (0.5>FIC≦4) in 14 of 27 strains. With a ciprofloxacin/ceftazidime combination, a synergistic effect was seen in 7 strains and an additive or indifferent effect in 20 strains. No antagonism (FIC>4) was seen with either combination. In addition, gemifloxacin/ceftazidime showed better MIC profiles against P. aerzginosa (MIC range: 0.063–1 μg/ml) than ciprofloxacin/ceftazidime (MIC range: 0.0634–4 μg/ml), even though gemifloxacin itself (MIC range: 0.25–32 μg/ml) was less potent than ciprofloxacin (MIC range: 0.13–16 μg/ml).

The test organisms were clinical isolates collected in Korea. Organisms were frozen at −70 C prior to testing. Testing was done by the checkerboard method in 96-well plates using Mueller-Hinton broth. Gemifloxacin and ciprofloxacin were tested at 13 concentrations (0.016–64 μg/ml), and ceftazidime was tested at 6 concentrations (1–32 μg/ml). Gemifloxacin or ciprofloxacin solution was dispensed alone in the first row and combined with ceftazidime in the remaining rows. Ceftazidime was also dispensed alone in the first row in the first column. Test strains of P. aeruginosa were grown for 18 h in Mueller-Hinton broth, and then these overnight cultures were diluted with the same fresh medium to the density of approximately $10^7$ CFU/mL. The bacterial concentrations were determined by measuring optical density or turbidity of the suspension and were verified by standard colony counts on antibiotic-free agar plates. A diluted bacterial solution was applied to 96-well plates containing serially diluted antimicrobial agents to yield $10^4$ CFU per spot. Plates were incubated aerobically overnight.

Minimal inhibitory concentrations (MICs) for each separate drug were determined. For wells along the growth-no growth interface, synergy was determined by calculating the Fractional Inhibitory Concentration (FIC) index. The Fractional Inhibitory Concentration (FIC) indices were calculated using the following formula:

$$FIC\,\text{index} = FIC_A + FIC_B = [A]/MIC_A + [B]/MIC_B$$

Wherein:

$FIC_{A(or\ B)}$, is the FIC of drug A (or B)

$MIC_{A\ (or\ B)}$ is the MIC of the organism to drug A (or B)

A (or B) is concentration of drug A (or B) that is the lowest inhibitory concentration The FIC indices were interpreted using the following criteria:

≦0.5=Synergy

>0.5–1.0=Additive

>1.0–4.0=Indifference

>4.0=Antagonism

The following gemifloxacin/ceftazidime combinations showed synergy against the noted P. aeruginosa strain:

| P. aeruginosa | gemifloxacin MIC µg/ml | ceftazidime MIC µg/ml | $C_{gemifloxacin}$ MIC µg/ml | $C_{ceftazidime}$ MIC µg/ml | $FIC_A$ | $FIC_B$ |
|---|---|---|---|---|---|---|
| 6003 | 1 | 4 | 0.25 | 1 | 0.25 | 0.25 |
| 6021 | 1 | 4 | 0.25 | 1 | 0.25 | 0.25 |
| 6030 | 1 | 4 | 0.125 | 1 | 0.13 | 0.25 |
| 6045 | 4 | 64 | 1 | 8 | 0.25 | 0.13 |
| 6047 | 8 | 64 | 1 | 2 | 0.13 | 0.03 |
| 6113 | 0.5 | 8 | 0.125 | 2 | 0.25 | 0.25 |
| 6123 | 1 | 4 | 0.125 | 1 | 0.13 | 0.25 |
| 6173 | 1 | 4 | 0.125 | 1 | 0.13 | 0.25 |
| P032 | 0.5 | 4 | 0.0625 | 1 | 0.13 | 0.25 |
| P036 | 8 | 32 | 1 | 4 | 0.13 | 0.13 |
| P039 | 2 | 8 | 0.5 | 2 | 0.25 | 0.25 |

Other gemifloxacin/ceftazidime combinations tested exhibited an additive or indifferent effect against other *P. aeruginosa* strains.

5) The synergistic activity of gemifloxacin or ciprofloxacin in combination with ceftazidime was investigated in 6 clinically isolated *P. aeruginosa* strains. The test organisms were clinical isolates collected in Korea. Organisms were frozen at −70 C. prior to testing. The combined effect of gemifloxacin or ciprofloxacin and ceftazidime was investigated by the checkerboard method in 96-well plates using Mueller-Hinton broth. Gemifloxacin and ciprofloxacin were tested at 12 concentrations (0.016–32 µg/ml), and ceftazidime was tested at 8 concentrations (0.25–32 µg/ml). Gemifloxacin or ciprofloxacin solution was dispensed alone in the first row and combined with ceftazidime in the remaining rows. Ceftazidime as also dispensed alone in the first row in the first column. Test strains of *P. aeruginosa* were grown for 18 h in Mueller-Hinton broth, and then these overnight cultures were diluted with the same fresh medium to the density of approximately $10^7$ CFU/mL. The bacterial concentrations were determined by measuring optical density or turbidity of the suspension and were verified by standard colony counts on antibiotic-free agar plates. A diluted bacterial solution was applied to 96-well plates containing serially diluted antimicrobial agents to yield $5 \times 10^5$ CFU/mL. Plates were incubated at 35 C for 18 hours.

MICs for each separate drug were determined, and for wells along the growth-no growth interface, synergy was determined by calculating FIC Indices as in Example 4. FIC Indices were calculated and interpreted as in Example 4.

Combinations of gemifloxacin/ceftazidime were synergistic for *P. aeruginosa* 6168, P003, and 6140.

provide an antibacterial regimen which has a broader spectrum of activity than either agent alone. In particular, such combinations exhibit synergistic activity against several clinical isolates of *Pseudomonas aeruginosa*, as well as reference strains of *Enterococcus faecalis, Staphylococcus saprophyticus*, or *Escherichia coli*, relative to either agent alone.

What is claimed is:

1. A method of treating bacterial infections caused by at least one of *Pseudomonas aeruginosa, E. faecalis* and *E. coli*, which method comprises
    simultaneous or sequential administration to a patient in need thereof, of a synergistic amount of gemifloxacin or a salt thereof and at least one cephalo-sporin selected from the group consisting of cefotaxime, ceflacor and ceftazidime.

2. The method according to claim 1, wherein said gemifloxacin is gemifloxacin mesylate.

3. The method according to claim 1, wherein the cephalo-sporin is cefotaxime.

4. The method according to claim 1, wherein the cephalo-sporin is ceftazidime.

5. The method according to claim 1, wherein gemifloxacin or a salt thereof and cephalo-sporin are administered in a ratio of from about 10:1 to about 1:10 (W/W).

6. The method according to claim 1, in which of gemifloxacin or a salt thereof and cephalo-sporin are administered simultaneously.

| P. aeruginosa | gemifloxacin MIC µg/ml | ceftazidime MIC µg/ml | $C_{gemifloxacin}$ MIC µg/ml | $C_{ceftazidime}$ MIC µg/ml | $FIC_A$ | $FIC_B$ |
|---|---|---|---|---|---|---|
| 6168 | 0.5 | 32 | 0.0625 | 2 | 0.13 | 0.06 |
| P003 | 2 | 32 | 0.125 | 2 | 0.06 | 0.06 |
| 6140 | 8 | 32 | 0.5 | 8 | 0.06 | 0.25 |

Combinations of gemifloxacin/ceftazidime tested exhibited an additive effect against *P. aeruginosa* 6016, 6156, and PA018R.

INDUSTRIAL APPLICABILITY

According to the present invention, combinations of gemifloxacin or a salt thereof and a β-lactam antibiotic 7. The method according to claim 6, achieved by the co-administration of separate compositions comprising gemifloxacin or a salt thereof and a cephalo-sporin.

8. The method according to any one of claims 1, 2, 3, 4 or 6, wherein the bacterial infection is caused by *Pseudomonas aeruginosa*.

* * * * *

UNITED STATES PATENT AND TRADEMARK OFFICE
CERTIFICATE OF CORRECTION

PATENT NO.        : 7,169,792 B2
APPLICATION NO.   : 10/496809
DATED             : January 30, 2007
INVENTOR(S)       : Nancy Niconovich et al.

It is certified that error appears in the above-identified patent and that said Letters Patent is hereby corrected as shown below:

Please insert the U.S. provisional application information on the title page as follows:

<u>Title Page</u>

Item (60) insert the following:
--Provisional Application No. 60/344,495, filed on November 30, 2001.--

Signed and Sealed this

First Day of May, 2007

JON W. DUDAS
*Director of the United States Patent and Trademark Office*